United States Patent [19]

Iwata et al.

[11] Patent Number: 5,703,068

[45] Date of Patent: *Dec. 30, 1997

[54] PENEM COMPOUNDS

[75] Inventors: Hiromitsu Iwata; Takashi Nakatsuka, both of Osaka; Rie Tanaka, Ibaraki; Masaji Ishiguro, Takarazuka, all of Japan

[73] Assignee: Suntory Limited, Osaka, Japan

[ * ] Notice: The term of this patent shall not extend beyond the expiration date of Pat. No. 5,506,225.

[21] Appl. No.: 971,827

[22] PCT Filed: Aug. 16, 1991

[86] PCT No.: PCT/JP91/01100

§ 371 Date: Feb. 19, 1993

§ 102(e) Date: Feb. 19, 1993

[87] PCT Pub. No.: WO92/03444

PCT Pub. Date: Mar. 5, 1992

[30] Foreign Application Priority Data

Aug. 20, 1990 [JP] Japan ................................. 2-218543

[51] Int. Cl.$^6$ ..................... C07D 499/00; A61K 31/43
[52] U.S. Cl. ................................. 514/195; 540/310
[58] Field of Search ...................... 540/310; 514/195

[56] References Cited

U.S. PATENT DOCUMENTS

| | | |
|---|---|---|
| 4,479,947 | 10/1984 | Christensen . |
| 4,654,331 | 3/1987 | Christensen . |
| 5,036,063 | 7/1991 | Lattrell et al. .................. 514/192 |
| 5,116,832 | 5/1992 | Ishiguro et al. ................ 540/310 |

FOREIGN PATENT DOCUMENTS

| | | |
|---|---|---|
| 0039 477 | 11/1981 | European Pat. Off. . |
| 0146 626 | 7/1985 | European Pat. Off. . |
| 0 199 446 | 10/1986 | European Pat. Off. . |
| 0252 885 | 1/1988 | European Pat. Off. . |
| 0273 747 | 7/1988 | European Pat. Off. . |
| 0275 002 | 7/1988 | European Pat. Off. . |
| 0295 100 | 12/1988 | European Pat. Off. . |

2 220 203 1/1990 United Kingdom .

OTHER PUBLICATIONS

Bioreversible Carriers in Drug Design: Theory and Application, Pergamon Press, 1987, pp. 13–16, Hans Bundgaard, "Design of Bioreversible Drug Derivatives and the Utility of the Double Prodrug Concept".

Chem. Pharm. Bull. vol. 38, No. 4, 1990, pp. 1077–1078, I. Miyauchi, et al., "Studies on Penem and Carbapenem. II. An Improved Synthesis of Orally Active Penem Antibiotic (5-Methyl-2-oxo-1,3-dioxol-4-yl)methyl (5R,6S)-2-(2-fluoroethylthio)-6-{(1R)-1-Hydroxyethyl}penem-3-Carboxylate".

*Primary Examiner*—Mukund J. Shah
*Assistant Examiner*—King Lit Wong
*Attorney, Agent, or Firm*—Oblon, Spivak, McClelland, Maier & Neustadt, P.C.

[57] ABSTRACT

Antibiotic penem compounds are represented by the following formula:

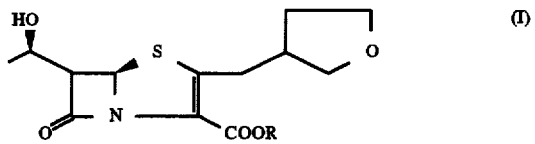

wherein R represents a group of the following formula:

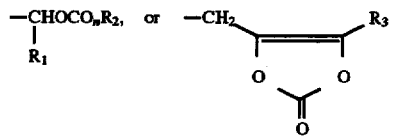

in which $R_1$ is a linear or branched, $C_1$–$C_6$ alkyl group, $R_2$ is a particular substituted or unsubstituted alkyl, aryl or aralkyl group, n is an integer of 1 or 2, and $R_3$ represents a specific substituted or unsubstituted alkyl, aryl or aralkyl group. Antibiotic compositions for oral administration are also described.

14 Claims, No Drawings

PENEM COMPOUNDS

This is a 371 application of PCT/JP91/01100, Aug. 16, 1991.

TECHNICAL FIELD

The present invention relates to penem compounds, and more specifically to penem compounds which are expected to find clinical utility as promising antibiotics.

BACKGROUND ART

The present inventors previously found that a group of penem compounds represented by the following formula (IV):

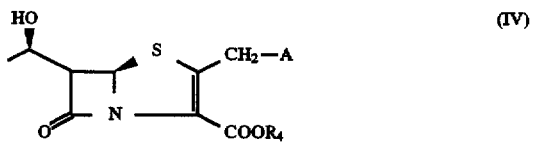

in which $R_4$ is a hydrogen atom or allyl group,

A is a 5- or 6-membered heterocyclic aliphatic group containing 1 or 2 oxygen atoms in the ring thereof and their pharmacologically acceptable salts have excellent antibacterial activities against both gram-positive and gram-negative, aerobic or anaerobic bacteria (Japanese Patent Publication No. 162694/1988).

Of these compounds, compounds represented by the following formula (V):

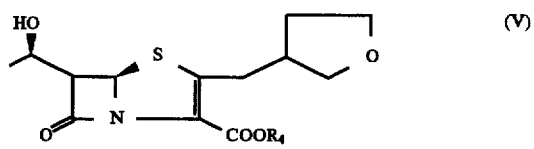

have high antibacterial activities and their high safety has been confirmed by their safety test in which laboratory animals were used. Their development as medical drugs is therefore expected.

The bioavailability of the compounds (V) is, however, not sufficient, so that their use as oral preparations requires improvements in their oral absorption.

DISCLOSURE OF INVENTION

The present inventors have carried out an extensive investigation on the compounds (V) with a view toward making improvements in their bioavailability. As a result, it has been found that protection of their carboxyl group with a particular ester-forming group can significantly improve their bioavailability, leading to the completion of the present invention.

The present invention provides a penem compound of the following formula (I):

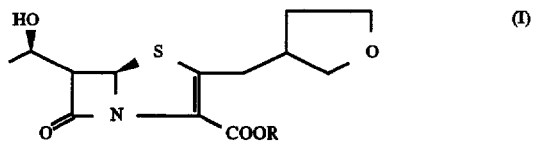

wherein R represents a group of the following formula (II) or (III):

in which $R_1$ is a hydrogen atom or a linear or branched, $C_1$–$C_6$ alkyl group or together with $R_2$; forms an o-phenylene group;

$R_2$ is a $C_1$–$C_6$ alkyl group, a $C_6$–$C_{10}$ aryl group, a $C_7$–$C_{11}$ aralkyl group, or a said $R_2$ group substituted by one or more substituents selected from $C_1$–$C_6$ alkyl groups, $C_6$–$C_{10}$ aryl groups, $C_7$–$C_{11}$ aralkyl groups, hydroxyl groups, $C_1$–$C_6$ alkoxyl groups and halogen atoms; and n is an integer of 1 or 2, or

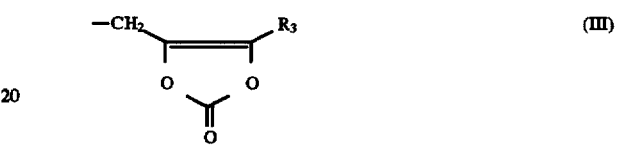

in which $R_3$ represents a $C_1$–$C_6$ alkyl group, a $C_6$–$C_{10}$ aryl group, a $C_7$–$C_{11}$ aralkyl group, or a said $R_3$ group substituted by one or more substituents selected from $C_1$–$C_6$ alkyl groups, $C_6$–$C_{10}$ aryl groups, $C_7$–$C_{11}$ aralkyl groups, $C_1$–$C_6$ alkoxyl groups and halogen atoms.

BEST MODE FOR CARRYING OUT THE INVENTION

The penem compound (I) of the present invention can be synthesized, for example, by reacting a halogenated alkyl compound (VI) with a penem compound (V') in accordance with the following formula:

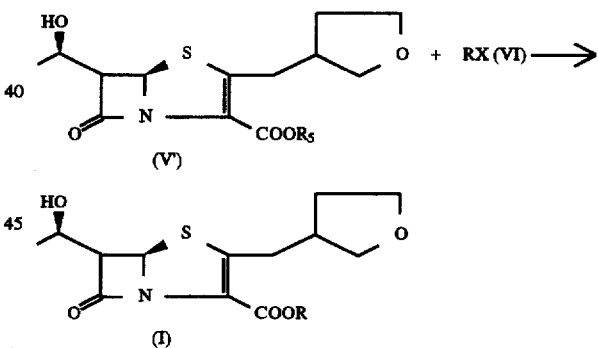

wherein

X represents a halogen atom, $R_5$ represents a hydrogen or alkali metal atom or an amino residuum, and R has the same meaning as defined above.

When $R_5$ in the compound (V') is an alkali metal atom or an amino residuum in the present invention, the target product can be obtained by stirring the compound (V') with the halogenated alkyl compound (VI) in an organic solvent.

When $R_5$ in the compound (V') is a hydrogen atom, on the other hand, the compound (V') is first reacted with an alkali metal hydroxide, an alkali metal salt or an amine compound in an organic solvent to form a salt, and the reaction mixture is then reacted with the halogenated alkyl compound (VI).

The halogenated alkyl compound represented by the formula (VI) can efficiently esterify the carboxyl group of the compound (V') with the group R to produce the target compound of the formula (I). Examples of the compound (VI) include those employed for the preparation of prodrugs of the penicillin or cephalosporin type: Described more specifically, there are those containing, as the group R, an acetyloxymethyl group, a 1-(acetyloxy)ethyl group, a pivaloyloxymethyl group, a 1-(ethoxycarbonyloxy)ethyl group, a 1-(isopropyloxycarbonyloxy)ethyl group, a 1-(cyclohexyloxycarbonyloxy) group, a 3-phthalidyl group, a (5-methyl-2-oxo-1,3-dioxolen-4-yl)methyl group or the like and, as the halogen atom represented by X, a chlorine, bromine or iodine atom.

No particular limitation is imposed on the alkali metal insofar as it forms a salt with the compound (V'). Examples of the alkali metal include lithium, sodium and potassium. Examples of their hydroxides and salts include sodium hydroxide, potassium hydroxide, sodium bicarbonate, sodium carboxylate, potassium bicarbonate and potassium carbonate. Exemplary amine compounds include ammonia, triethylamine, and diisopropyl ethyl amine.

No particular limitation is imposed on the reaction solvent. Examples of the reaction solvent include aromatic hydrocarbons such as toluene and xylene, aliphatic hydrocarbons such as pentane and hexane, halogenated alkyls such as methylene chloride and chloroform, halogenated aryls such as chlorobenzenes, ketones such as acetone and methyl ethyl ketone, nitriles such as acetonitrile and propionitrile, amides such as dimethylformamide, sulfoxides such as dimethyl sulfoxide, ethers such as diethyl ether and tetra-hydrofuran, and alcohols such as isopropanol and t-butanol. They can be used either singly or in combination.

The reaction may be carried out at room temperature or, when desired, under heating at a temperature below 80° C. The reaction time is generally 1–48 hours although it varies depending on the halogenated alkyl compound (VI) to be used.

The penem compound (I) obtained as described above may be used as is but, in general, is purified, as needed, by a method such as column chromatography or recrystallization for use as a medicine.

For oral, parenteral or external administration, the compounds according to the present invention can be formulated as antibiotics in a manner known per se in the art.

Although the dosage of each penem derivative of the present invention varies depending on many factors, the typical daily dosage ranges from 50 mg to 3 g for standard adults with the administration of 100 mg to 2 g in divided portions being preferred. In general, the above dosage will be administered in the form of a dosage unit which contains an appropriate amount of the active ingredient and a suitable, physiologically-acceptable carrier or extender.

For oral administration, tablets or capsules can be used. They may contain—together with the active ingredient—an extender, e.g., lactose, glucose, sucrose, mannitol, sorbitol or cellulose, and a lubricant, e.g., talc, stearic acid or a stearate salt. Tablets may additionally contain a binder, for example, hydroxypropyl cellulose or starch.

The compounds according to the present invention can be used not only for men but also for animals.

The present invention will hereinafter be described more specifically by the following examples. It is however borne in mind that the present invention is not limited at all by these examples.

EXAMPLE 1

1-(Cyclohexyloxycarbonyloxy)ethyl (5R,6S)-6-[(R)-1-hydroxyethyl]-2-(3-tetrahydrofuryl)methylpenem-3-carboxylate (Compound 7):

The mixture of sodium (5R,6S)-6-[(R)-1-hydroxy-ethyl]-2-(3-tetrahydrofuryl)methylpenem-3-carboxylate 2.5 hydrate (Compound 1, 1 g), 1-chloroethyl cyclohexylcarbonate (0.6 ml) and N,N-dimethylformamide (6 ml) was heated at 70° C. for one hour.

The reaction mixture was then diluted with ethyl acetate and washed with water. The organic layer was dried and then concentrated. The residue was purified by passing it through a silica gel column, whereby 0.32 g of the title compound was obtained.

EXAMPLE 2

Acetyloxymethyl (5R,6S)-6-[(R)-1-hydroxyethyl]-2-(3-tetrahydrofuryl)methylpenem-3-carboxylate (Compound 2):

Sodium (5R,6S)-6-[(R)-1-hydroxyethyl]-2-(3-tetrahydrofuryl)methylpenem-3-carboxylate 2.5 hydrate (Compound 1, 2.93 g) was dissolved in N,N-dimethylformamide (40 ml), to which acetyloxymethyl bromide (1.47 g) was added dropwise under ice-cooling and stirring, followed by stirring at room temperature for further 1.5 hours. The reaction mixture was then diluted with ethyl acetate (300 ml) and washed twice with water (200 ml). The organic layer was dried and concentrated. The residue was purified by passing it through a silica gel column, whereby 1.3 g of the title compound were obtained.

EXAMPLE 3

Phthalidyl (5R,6S)-6-[(R)-1-hydroxyethyl]-2-(3-tetrahydrofuryl)methylpenem-3-carboxylate (Compound 8):

The mixture of sodium (5R,6S)-6-[(R)-1-hydroxyethyl]-2-(3-tetrahydrofuryl)methylpenem-3-carboxylate 2.5 hydrate (Compound 1, 2.93 g), bromophthalide (2.8 g) and dimethyl sulfoxide (30 ml) was stirred at room temperature for 10 minutes. The reaction mixture was diluted with ethyl acetate, followed by washing with water. The organic layer was dried and then concentrated. The residue was purified by passing it through a silica gel column, whereby 2.3 g of the title compound were obtained.

EXAMPLE 4

(5-Methyl-2-oxo-1,3-dioxolen-4-yl)methyl (5R,6S)-6-[(R)-1-hydroxyethyl]-2-(3-tetrahydrofuryl)methylpenem-3-carboxylate (Compound 9):

The mixture of sodium (5R,6S)-6-[(R)-1-hydroxyethyl]-2-(3-tetrahydrofuryl)methylpenem-3-carboxylate 2.5 hydrate (Compound 1, 4 g), 4-iodomethyl-5-methyl-2-oxo-1,3-dioxolene (7.6 g) and N,N-dimethylformamide (40 ml) was stirred at room temperature for 2.5 hours. The reaction mixture was diluted with ethyl acetate, followed by washing with water. The organic layer was dried and then concentrated. The residue was purified by passing it through a silica gel column. An oil so obtained was recrystallized from hexane, whereby 1.47 g of the title compound were obtained.

EXAMPLES 5–8

In each example, sodium (5R,6S)-6-[(R)-1-hydroxyethyl]-2-(3-tetrahydrofuryl) methylpenem-3-carboxylate 2.5 hydrate (Compound 1) was reacted with the corresponding halogenated alkyl compound (acyloxymethyliodide), which is shown in Table 1, and N,N-dimethylformamide as in Example 1, whereby the corresponding compound (I) of the present invention, whose R group is also shown in Table 1, was obtained. The reaction time required and the yield in the reaction are also shown in Table 1.

In addition, physicochemical data of the compounds obtained in Examples 5–8 are shown in Table 2, together with those of the compounds obtained in Examples 1–4.

Each test compound (30 μmole/kg) was orally administered to SD strain rats (three male rats per group). Urine was collected over 6 hours from the administration, and the

TABLE 1

| Example No. | Comp'd No. | Halogenated alkyl compound | R in the compound (I) | Reaction time (hours) | Yield (%) |
|---|---|---|---|---|---|
| 5 | 3 | $ICH(CH_3)OCOCH_3$ | $-CH(CH_3)OCOCH_3$ | 2.5 | 30 |
| 6 | 4 | $ICH_2OCOC(CH_3)_3$ | $-CH_2OCOC(CH_3)_3$ | 2 | 60 |
| 7 | 5 | $ICH(CH_3)OCOOC_2H_5$ | $-CH(CH_3)OCOOC_2H_5$ | 3 | 27 |
| 8 | 6 | $ICH(CH_3)OCOOCH(CH_3)_2$ | $-CH(CH_3)OCOOCH(CH_3)_2$ | 2 | 52 |

TABLE 2(1)

| Comp'd No. | Compound | Appearance | $IR_{max}^{neat}$ ($cm^{-1}$) | NMR ($CDCl_3$) |
|---|---|---|---|---|
| 2 | Acetyloxymethyl (5R,6S)-6-[(R)-1-hydroxyethyl]-2-(3-tetrahydrofuryl)methyl-penem-3-carboxylate | Pale yellow oil | 3450, 1786 1765, 1719 1570 | 1.36(3H, d, J=7Hz), 1.54–1.72(1H, m), 1.99–1.19(1H, m), 2.13(3H, m), 2.35–2.51(1H, m), 2.72–3.13(2H, m), 3.36–3.52(1H, m), 3.68–3.98(4H, m), 4.18–4.31(1H, m), 5.60(1H, s), 5.82 & 5.86(each, 1H, d, J=5Hz) |
| 3 | 1-(Acetyloxy)ethyl (5R,6S)-6-[(R)-1-hydroxyethyl]-2-(3-tetrahydrofuryl)methyl-penem-3-carboxylate | Yellow oil | 3388, 1787 1762, 1715 1573 | 1.35 & 1.36(each, 3/2H, d, J=6Hz), 1.53 & 1.54 (each, 3/2H, d, J=6Hz), 2.50–2.71(1H, m), 1.90 & 1.91(each, 1/2H, d, J=4Hz), 1.99–2.16 (1H, m), 2.08(3H, d, J=6Hz), 2.37–2.54(1H, m), 2.64–3.18(2H, m), 2.38–2.50(1H, m), 3.65–3.95 (4H, m), 4.18–4.30(1H, m), 5.59(1H, s), 6.96(1H, q, J=6Hz) |
| 4 | Pivaloyloxymethyl (5R,6S)-6-[(R)-1-hydroxyethyl]-2-(3-tetrahydrofuryl)methylpenem-3-carboxylate | Yellow oil | 3414, 1790 1754, 1723 1574 | 1.22(9H, s), 1.35(3H, d, J=7Hz), 1.52–1.72(1H, m), 1.97–2.15(2H, m), 2.38–2.52(1H, m), 2.69–3.13(2H, m), 3.37–3.49(1H, m), 3.67–3.94(4H, m), 4.18–4.30 (1H, m), 5.60(1H, s), 5.83 & 5.90(each, 1H, d, J=6Hz) |
| 5 | 1-(Ethoxycarbonyloxy)ethyl (5R,6S)-6-[(R)-1-hydroxy-ethyl]-2-(3-tetrahydrofuryl)-methylpenem-3-carboxylate | Colorless oil | 3408, 1787 1762, 1718 1576 | 1.26–1.40(6H, m), 1.51–1.73(4H, m), 1.80 & 1.83(each, 1/2H, d, J=5Hz), 2.00–2.16(1H, m), 2.39–2.53(1H, m), 2.62–3.19(2H, m), 3.38–3.51 (1H, m), 3.67–3.95(4H, m), 4.16–4.31(3H, m) 5.58(1H, s), 6.82–6.90(1H, m) |

TABLE 2(2)

| Comp'd No. | Compound | Appearance | $IR_{max}^{neat}$ ($cm^{-1}$) | NMR ($CDCl_3$) |
|---|---|---|---|---|
| 6 | 1-(Isopropyloxycarbonyloxy)-ethyl (5R,6S)-6-[(R)-1-hydroxy-ethyl]-2-(3-tetrahydrofuryl)]-methylpenem-3-carboxylate | Pale yellow oil | 3408, 1790 1760, 1716 1574 | 1.23–1.40(9H, m), 1.50–1.71(4H, m), 1.83 & 1.86 (each, 1/2H, d, J=4Hz), 1.98–2.15(1H, m), 2.39–2.51(1H, m), 2.62–3.18(2H, m), 3.38–3.50(1H, m), 3.65–3.95(4H, m), 4.16–4.29(1H, m), 4.84–4.99(1H, m), 5.58(1H, s), 6.81–6.90(1H, m) |
| 7 | 1-(Cyclohexyloxycarbonyloxy)ethyl (5R,6S)-6-[(R)-1-hydroxyethyl]-2-(3-tetrahydrofuryl)methylpenem-3-carboxylate | Yellow oil | 3400, 2938 1791, 1756 1258, 1074 | 1.30–2.15(18H, m), 2.40–2.53(1H, m), 2.60–3.20(2H, m), 3.40–3.50(1H, m), 3.68–3.73(1H, m), 3.75–3.95(3H, m), 4.20–4.28(1H, m), 4.60–4.72(1H, m), 5.58(1H, s), 6.83–6.90(1H, m) |
| 8 | Phthalidyl (5R,6S)-6-[(R)-1-hydroxyethyl]-2-(3-tetrahydrofuryl)methylpenem- | Colorless crystal | 3400, 1787 1719, 972 | 1.30–1.35(3H, d), 1.40–1.70(1H, m), 1.90–2.15(1H, m), 2.35–2.55(1H, m), 2.65–3.20(2H, m), 3.30–3.52(1H, m), 3.70–3.95(4H, m), 4.15–4.25(1H, m), 5.58–5.60(1H, m), 7.43(1/2H, s), 7.49(1/2H, s) |
| 9 | (5-Methyl-2-oxo-1,3-dioxolane-4-yl)methyl (5R,6S)-6-[(R)-1-hydroxymethyl]-2-(3-tetrahydro-furyl)methylpenem-3-carboxylate | Colorless crystal | 3400, 1821 1789, 1710 1318 | 1.37(3H, d, J=6Hz), 1.55–1.70(1H, m), 2.00–2.15 (1H, m), 2.20(3H, s), 2.40–2.50(1H, m), 2.70–3.10 (2H, m), 3.40–3.50(1H, m), 3.71(1H, dd, J=1Hz, 3Hz), 3.78(1H, t, J=8Hz), 3.85–3.92(1H, m), 4.20–4.30(1H, m), 4.95(1H, s,), 4.98(1H, s), 5.60(1H, d, J=1Hz) |

EXAMPLE 9

The bioavailability of certain compounds (I) of the present invention was tested relying upon their recovery rates in urine.

recovery rate of the corresponding compound present in the urine was determined by bioassay. The results are shown below.

TABLE 3

| Comp'd No. | R in the compound (I) | Urinary Recovery (%) | Ratio |
|---|---|---|---|
| 1 | Na | 2.85 | 1 (Control) |
| 2 | $-CH_2OCOCH_3$ | 22.87 | 8.0 |
| 3 | $-CH(CH_3)OCOCH_3$ | 28.95 | 10.2 |
| 4 | $-CH_2OCOC(CH_3)_3$ | 24.23 | 8.5 |
| 5 | $-CH(CH_3)OCOOC_2H_5$ | 20.97 | 7.4 |
| 6 | $-CH(CH_3)OCOOCH(CH_3)_2$ | 22.40 | 7.9 |
| 7 | | 22.27 | 7.8 |
| 8 | 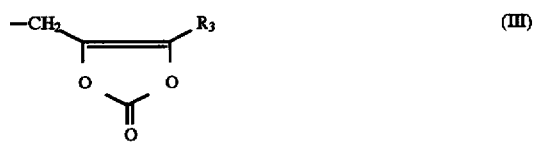 | 35.55 | 12.5 |
| 9 | 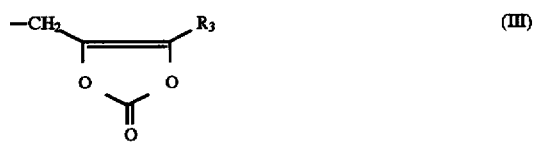 | 28.46 | 10.0 |

As is apparent from these results, the compounds (I) of the present invention showed higher recovery rates in urine, namely, higher bioavailability compared with the penem compound (V).

PREPARATION EXAMPLES

In each of the following preparation examples, the active ingredient may be, for example, Compound 8 or an equivalent amount of any one of the other compounds of the present invention.

Preparation 1

Capsules

| Ingredient No. | Ingredient | mg/capsule |
|---|---|---|
| 1 | Invention compound | 150 |
| 2 | Lactose | 20 |
| 3 | Magnesium stearate | 4 |
| | (Total) | 174 mg |

(Production procedures)

Ingredients 1 and 2 were combined together in a suitable mixer, to which Ingredient 3 was added, followed by further mixing. The resultant mixture was filled into capsules using a capsule filling machine.

Preparation 2

Tablets

| Ingredient No. | Ingredient | mg/tablet |
|---|---|---|
| 1 | Invention compound | 150 |
| 2 | Crystalline cellulose | 50 |
| 3 | Calcium carboxymethylcellulose | 10 |
| 4 | Magnesium stearate | 4 |
| | (Total) | 214 mg |

(Production procedures)

Ingredients 1–3 were combined together in a suitable mixer, to which Ingredient 4 was added, followed by mixing for additional several minutes. The resultant mixture was compressed into tablets of a predetermined size and weight by a tableting machine.

INDUSTRIAL APPLICABILITY

As has been described above, the compounds (I) of the present invention exhibit excellent bioavailability so that they can be advantageously used as oral antibiotics.

We claim:

1. A penem compound of the following formula (I):

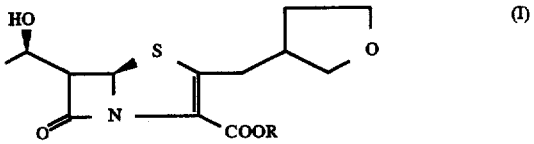

wherein

R represents a group of the following formula (II) or (III):

in which

R₁ is a hydrogen atom or a linear or branched, $C_1$–$C_6$ alkyl group or, together with $R_2$, forms an o-phenylene group;

$R_2$ is a $C_1$–$C_6$ alkyl group, a $C_6$–$C_{10}$ aryl group, a $C_7$–$C_{11}$ aralkyl group, said $R_2$ group or a substituted by one or more substituents selected from $C_1$–$C_6$ alkyl groups, $C_6$–$C_{10}$ aryl groups, $C_7$–$C_{11}$ aralkyl groups, hydroxyl groups, $C_1$–$C_6$ alkoxyl groups and halogen atoms; and n is an integer of 1 or 2, or

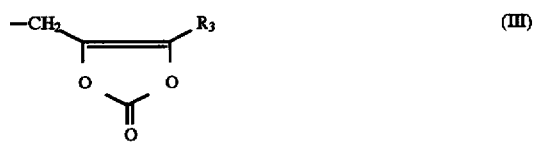

in which $R_3$ represents a $C_1$–$C_6$ alkyl group, a $C_6$–$C_{10}$ aryl group, a $C_7$–$C_{11}$ aralkyl group, or a said $R_3$ group substituted by one or more substituents selected from $C_1$–$C_6$ alkyl groups, $C_6$–$C_{10}$ aryl groups, $C_7$–$C_{11}$ aralkyl groups, hydroxyl groups, $C_1$–$C_6$ alkoxyl groups and halogen atoms.

2. A compound according to claim 1, wherein $R_1$ represents a hydrogen atom, a methyl group or, together with the remainder of R, forms a 3-phthalidyl group.

3. A compound according to claim 1, wherein $R_2$ represents a $C_1$–$C_6$ alkyl group.

4. A compound according to claim 1, wherein R represents an acetyloxymethyl group.

5. A compound according to claim 1, wherein R represents a 1-(acetyloxy) ethyl group.

6. A compound according to claim 1, wherein R represents a pivaloyloxymethyl group.

7. A compound according to claim 1, wherein R represents a 1-(ethoxycarbonyloxy) ethyl group.

8. A compound according to claim 1, wherein R represents a 1-(isopropyloxycarbonyloxy) ethyl group.

9. A compound according to claim 1, wherein R represents a 1-(cyclohexyloxycarbonyloxy) ethyl group.

10. A compound according to claim 1, wherein R represents a 3-phthalidyl group.

11. A compound according to claim 1, wherein R represents a (5-methyl-2-oxo-1,3-dioxolen-4-yl)methyl group.

12. A compound according to claim 1 which is selected from the group consisting of Acetyloxymethyl (5R,6S)-6-[(R)-1-hydroxyethyl]-2-(3-2-tetrahydrofuryl)methylpenem-3-carboxylate;

1-(Acetyloxy)ethyl (5R,6S)-6[(R)-1-hydroxyethyl]-2-(3-tetrahydrofuryl)methylpenem-3-carboxylate;

Pivaloyloxymethyl (5R, 6S)-6-[(R)-1-hydroxyethyl]-2-(3-tetrahydrofuryl)methylpenem-3-carboxylate;

1-(Ethoxycarbonyloxy)ethyl (5R, 6S) -6-[(R)-1-hydroxyethyl]-2-(3-tetrahydrofuryl)-methylpenem-3-carboxylate;

1-(Isopropyloxycarbonyloxy)ethyl (5R, 6S)-6-[(R)-1-hydroxyethyl]-2-(3-tetrahydrofuryl)methylpenem-3-carboxylate;

1-(Cyclohexyloxycarbonyloxy)ethyl (5R, 6S)-6-[(R)-1-hydroxyethyl]-2-(3-tetrahydrofuryl)methylpenem-3-carboxylate;

Phthalidyl (5R, 6S) -6-[(R) -1-hydroxyethyl]-2-(3-tetrahydrofuryl)methylpenem-3-carboxylate;

(5-Methyl-2-oxo-1,3-dioxolane-4-yl)methyl (5R, 6S)-6-[(R)-1-hydroxyethyl]-2-(3-tetrahydrofuryl)methylpenem-3-carboxylate.

13. An antibiotic composition, comprising an effective amount of a compound of the following formula (I):

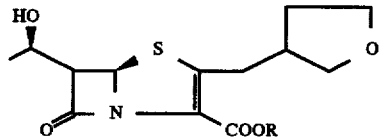
(I)

wherein
R represents a group of the following formula (II) or (III):

(II)

in which $R_1$ is a hydrogen atom or a linear or branched, $C_1$–$C_6$ alkyl group or, together with $R_2$, forms an o-phenylene group;

$R_2$ is a $C_1$–$C_6$ alkyl group, a $C_6$–$C_{10}$ aryl group, a $C_7$–$C_{11}$ aralkyl group, or a said $R_2$ group substituted by one or more substituents selected from $C_1$–$C_6$ alkyl groups, $C_6$–$C_{10}$ aryl groups, $C_7$–$C_{11}$ aralkyl groups, hydroxyl groups, $C_1$–$C_6$ alkoxyl groups and halogen atoms; and n is an integer of 1 or 2, or

(III)

in which $R_3$ represents a $C_1$–$C_6$ alkyl group, a $C_6$–$C_{10}$ aryl group, a $C_7$–$C_{11}$ aralkyl group, or a said R3 group substituted by one or more substituents selected from $C_1$–$C_6$ alkyl groups, $C_6$–$C_{10}$ aryl groups, $C_7$–$C_{11}$ aralkyl groups, hydroxyl groups, $C_1$–$C_6$ alkoxyl groups and halogen atoms, and a pharmaceutically-acceptable carrier.

14. A method of treating a subject with an antibiotic, comprising:

orally administering the composition of claim 13 to said subject.

* * * * *